(12) United States Patent
Al-Hafez

(10) Patent No.: US 6,361,566 B1
(45) Date of Patent: Mar. 26, 2002

(54) HIP PROSTHESIS

(76) Inventor: Bashar Al-Hafez, 38, Vimy Avenue, Apt. 302, Halifax, Nova Scotia (CA), B3M 1G6

( * ) Notice: Subject to any disclaimer, the term of this patent is extended or adjusted under 35 U.S.C. 154(b) by 0 days.

(21) Appl. No.: 09/522,932

(22) Filed: Mar. 10, 2000

(51) Int. Cl.$^7$ ................................................. A61F 2/32
(52) U.S. Cl. .................. 623/22.15; 623/22.4
(58) Field of Search ................ 623/22.11–22.46, 623/23.11–23.46

(56) References Cited

U.S. PATENT DOCUMENTS

| | | | |
|---|---|---|---|
| 3,894,297 A | * | 7/1975 | Mittelmeier et al. ............... 3/1 |
| 4,115,875 A | | 9/1978 | Rambert et al. |
| 4,430,761 A | * | 2/1984 | Niederer et al. .............. 3/1.91 |
| 4,530,114 A | | 7/1985 | Tepic |
| 4,693,724 A | * | 9/1987 | Rhenter et al. ................ 623/23 |
| 4,795,472 A | | 1/1989 | Crowninshield et al. |
| 4,938,773 A | | 7/1990 | Strand |
| 4,963,155 A | | 10/1990 | Lazzeri et al. |
| 5,002,578 A | | 3/1991 | Luman |
| 5,258,035 A | | 11/1993 | Hofmann et al. |
| 5,286,260 A | | 2/1994 | Bolesky et al. |
| 5,443,520 A | * | 8/1995 | Zweymuller et al. ......... 623/22 |
| 5,879,398 A | * | 3/1999 | Swarts et al. .................. 623/22 |
| 6,146,425 A | * | 11/2000 | Hoermansdoerfer ..... 623/22.31 |
| 6,162,257 A | * | 12/2000 | Gustilo et al. ........... 623/22.32 |
| 6,231,612 B1 | * | 5/2001 | Balay et al. ............. 623/22.31 |

FOREIGN PATENT DOCUMENTS

| | | |
|---|---|---|
| CA | 1234452 | 3/1988 |
| CA | 1277451 | 12/1990 |
| CA | 1283251 | 4/1991 |
| CA | 1283755 | 5/1991 |
| CA | 1302656 | 6/1992 |

* cited by examiner

*Primary Examiner*—Corrine McDermott
*Assistant Examiner*—Hieu Phan
(74) *Attorney, Agent, or Firm*—Swabey Ogilvy Renault

(57) ABSTRACT

There is disclosed a hip prosthesis to replace a damaged hip-joint. The hip prosthesis is intended to be disposed at one end thereof into a cup-shaped cavity of an acetabulum and at the other end thereof into a femur canal of a person suffering from a damaged hip-joint. The hip prosthesis comprises an acetabulum part having a cotyloid member to be tightly engaged into the acetabulum, an elongated neck part, and a femur part. The elongated neck part has an articulation head at one end thereon, the head being shaped to be articulately received in the acetabulum part, and a slidable connection at the other end thereof for engagement with the femur part. The femur part has a femur canal insertable portion formed with an arrangement to secure same in the femur canal by being embedded in regenerated bone marrow, and an engaging channel to receive the slidable connection of the elongated neck part and to securely connect the elongated neck part to the femur part.

15 Claims, 4 Drawing Sheets

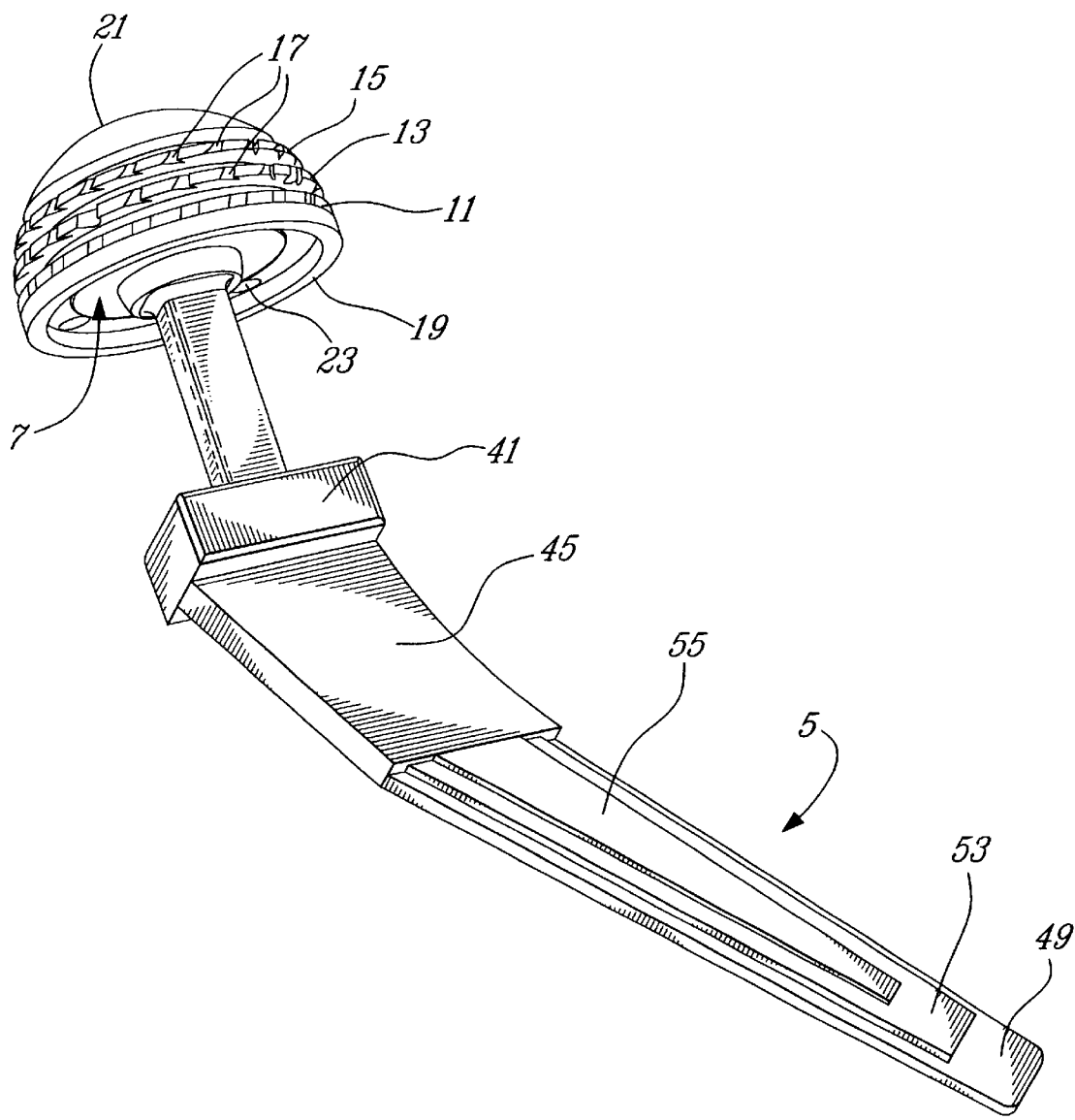

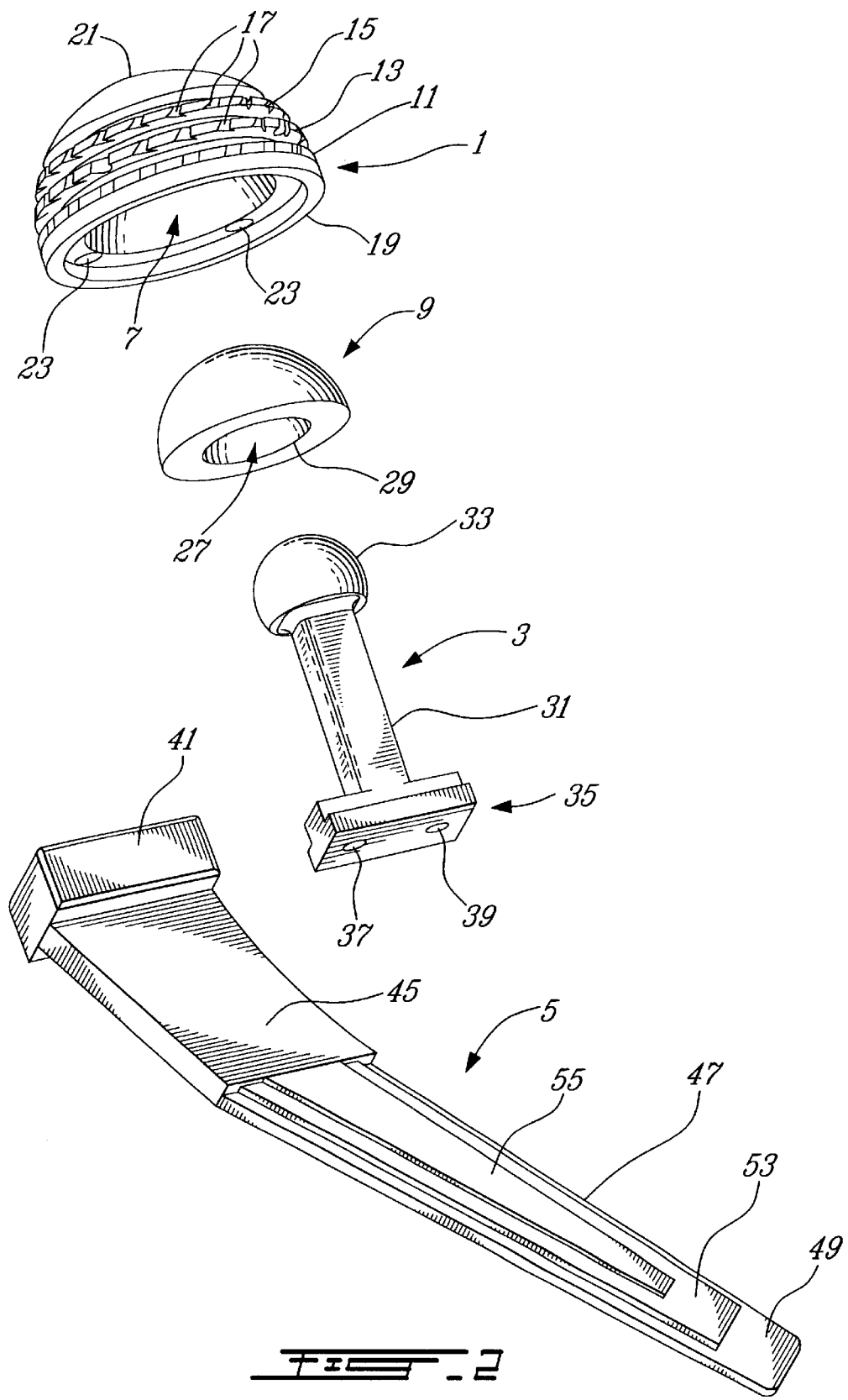

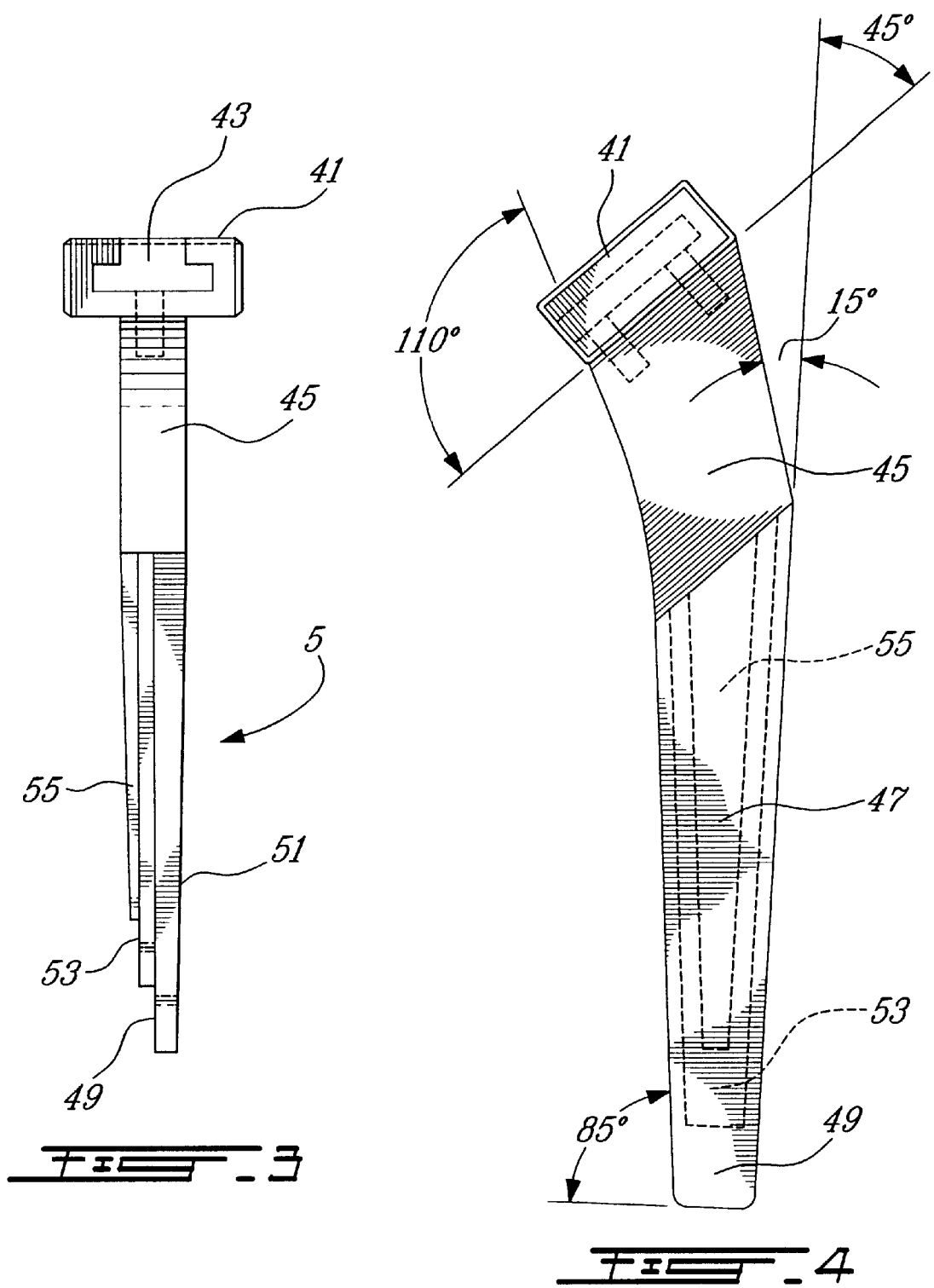

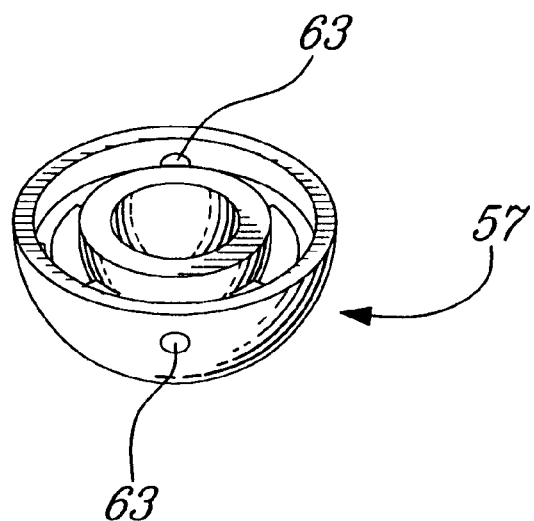
_FIG_5
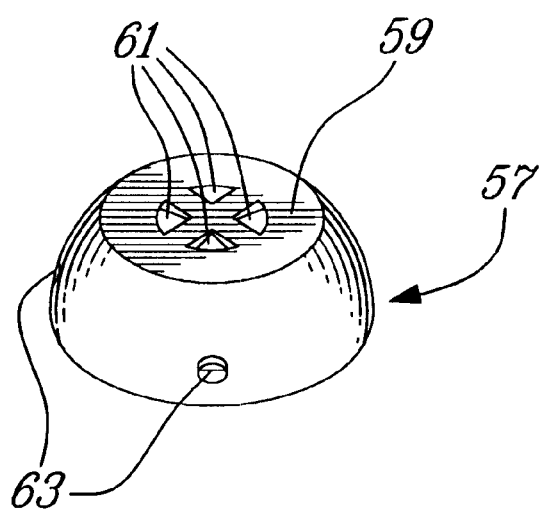
_FIG_6

HIP PROSTHESIS

BACKGROUND OF INVENTION (a) Field of the Invention

This invention relates to a hip prosthesis. More particularly, the invention is concerned with a hip prosthesis of the type that is designed to prevent unlocking thereof after surgery.

(b) Description of the Prior Art

In spite of the fact that there are many available hip prostheses that can be used to replace damaged hip joints, one is often faced with the problem that hip prostheses are sometimes subject to unlocking after surgery, either because the acetabulum part is not sufficiently fixed into the acetabulum or the femur part which is inserted in the femur canal is not sufficiently anchored therein. This is of course a serious problem, since if this should happen, a new surgery may have to be undertaken, and possibly a new hip prosthesis may have to be installed.

SUMMARY OF THE INVENTION

In order to overcome the above disadvantages, there is provided a hip prosthesis to replace a damaged hip-joint, the hip prosthesis to be disposed at one end thereof into a cup-shaped cavity of an acetabulum and at the other end thereof into a femur canal of a person suffering from a damaged hip-joint. The hip prosthesis comprises

- an acetabulum part comprising a cotyloid member and means for tightly engaging the cotyloid member into the acetabulum;
- an elongated neck part;
- a femur part;
- the elongated neck part having an articulation head at one end thereof, the head being shaped to be articulately received in the acetabulum part, and slidable connecting means at the other end thereof for engagement with the femur part;
- the femur part having a femur canal insertable portion formed with means to secure same in the femur canal by being embedded in regenerated bone marrow, and engaging means to receive the slidable connecting means of the elongated neck part and to securely connect the elongated neck part to the femur part.

The acetabulum part is preferably semi-spherical, and may be provided with a plurality of peripheral flanges capable of engaging with the acetabulum.

In accordance with a preferred embodiment, the peripheral flanges are each formed with a plurality of outwardly projecting points which may be regularly distributed along each flange, each projecting point forming an angle of between about 30 and 60°, preferably about 45° with respect to a tangent at the location of a respective projection point. Preferably, the projection points are oriented in a way to be engaged within the acetabulum when rotating the acetabulum part clockwise.

In accordance with yet another embodiment, the hip prosthesis according to the invention comprises a buffer member adapted to be fixedly mounted inside the acetabulum part, and to snappingly engage the articulated head. The buffer part is preferably semi-spherical, and provided with a cup-shaped cavity to receive the articulated head. It may be made of an inert material such as polyethylene, ceramic and an inert metallic substance. On the other hand, the preferred material of the acetabulum member is a titanium containing substance.

In accordance with yet another embodiment, the slidable connecting means of the elongated neck part comprises an inverted T-shaped portion which is perpendicular to the neck part, and the engaging means of the femur part comprises a slide member formed with an inverted T-shaped channel shaped to slidably receive the inverted T-shaped portion. The inverted T-shaped portion and the sliding member are normally adapted to be secured together by means of screws.

In accordance with yet another preferred embodiment, the femur part comprises a rectangular shaped shank portion joining the femur canal insertable portion and the slide member.

Preferably, the femur canal insertable portion comprises a first elongated pyramidal member extending from the shank portion, an elongated trapezoidal member shorter and narrower than first elongated trapezoidal member and projecting from first elongated pyramidal member, and a second elongated pyramidal member shorter and narrower than the trapezoidal member and tapering down from the shank portion to the opposite end thereon, the femur canal insertable portion thereby easily being embedded in the regenerated bone marrow.

In accordance with yet another embodiment, femur canal insertable portion angularly extends from the shank portion and the sliding member, for example the femur canal insertable portion extends from the shank portion at an angle of about 15° and from said sliding member at an angle of about 45°.

In accordance with yet another embodiment, the acetabulum part comprises a hollow truncated half sphere having a flat face, triangular openings being formed in the flat face to permit growth of bone cells into the hollow truncated half sphere, and screw holes along the lower edge of the hollow truncated half sphere oriented at about 45°. In this case, the buffer member is preferably spaced from the walls of the hollow truncated half sphere wherein bone cells can be permitted to grow.

BRIEF DESCRIPTION OF DRAWINGS

The invention will be understood more fully from the following detailed description of embodiments which are given only for the purpose of illustration and without limitation. In the drawings:

FIG. 1 is a perspective view of a hip prosthesis according to the invention;

FIG. 2 is an exploded view in perspective of the hip prosthesis illustrated in FIG. 1;

FIG. 3 is a side view of the femur part;

FIG. 4 is a top plan view of the femur part showing the angular arrangement of the various parts;

FIG. 5 is a perspective view of a modified acetabulum part according to the invention, showing the interior thereof; and FIG. 6 is a perspective view of the acetabulum part of FIG. 5 showing the exterior thereof.

DESCRIPTION OF PREFERRED EMBODIMENTS

With reference to the drawings, the hip prosthesis which is illustrated, generally comprises an acetabulum part 1, a neck part 3 and a femur part 5. Acetabulum part 1 appears as a semi-spherical cup-shaped element which, as will be appreciated by one skilled in the art, is shaped to fit exactly in the acetabulum (not illustrated) of a person who suffers from a damaged hip-joint.

More specifically, acetabulum part 1, has a semi-spherical cavity 7 therein to receive a buffer member 9 which will be described later. The outer surface of acetabulum part 1 has a series, here three, of peripheral flanges 11, 13, 15 formed by indenting outwardly projecting points 17 which all form an angle of about 30 to 60° preferably 45° with respect to the tangent at the location of a respective point, and project in the same direction. It will obviously be noted that from the edge 19 of acetabulum part 1 to base 21 thereof, flanges 11, 13, 15 are parallel to one another and decrease in diameter as shown. In order to fixedly dispose acetabulum part 1 within the cavity defined by the acetabulum (not shown) of a person suffering from a damaged hip-joint, it is placed therein and rotated clockwise where projecting points 17 will hold acetabulum part 1 firmly into the acetabulum without any possibility of becoming dislodged therefrom. Preferably, an antibiotic cement composition is also used.

To reinforce acetabulum part 1 in place within the cavity of the acetabulum, four screw holes 23 are provided along the lower edge of acetabulum part, at a 45° angle enabling screws (not shown) to penetrate surrounding bones (not shown) thereby further reinforcing acetabulum part 1 in place within the cavity of the acetabulum.

Although acetabulum part 1 can be made of any suitable material, experience has shown that it preferably should be made of a titanium containing compound, such as an alloy of titanium.

As mentioned before the acetabulum part includes buffer member 9 which is intended to receive the head of neck part 3 that will be described later. Buffer member 9 is also semi-spherical and is preferably made of an inert substance, such as polyethylene, ceramic of an inert metallic substance. In the illustrated embodiment, buffer member 9 is made of polyethylene. It is shaped to fit exactly within cavity 7 of acetabulum part 1 and is fixed therein by any known means, such by using an antibiotic cement. Any other means well known to those skilled in the art may also be used.

Buffer member 9 is formed with a partly-spherical cavity 27, with in turned lower edge 29, the latter intending to snappingly engage the head of neck part 3, as will be discussed later, while enabling the head to freely articulate therein.

Turning now to neck part 5, the latter will be seen to consist of an octagonal elongated member 31 (although any other cross-section could be used as will be appreciated by one skilled in the art) having an articulated head 33 at one end thereof and an inverted T-shaped connection 35 at the other end. More specifically, .it will be seen that connection 35 consists of an elongated member which is perpendicular to elongated member 31, and has an inverted T-shaped cross-section. Furthermore, in order to enable neck part 3 to be firmly fixed to femur part 5, the two parts are additionally screwed together as schematically illustrated by screw holes 37,39 appearing in connection 35. In practice, when buffer member 9 has been solidly mounted within cavity 7 of acetabulum part 1, neck part 3 is connected thereto by snapping engagement.

With reference to FIG. 3, the portion of femur part 5 which is adapted to be introduced into the femur canal, will now be described. It consists of a slide member 41 which has an inverted T-shaped channel 43 formed therein and shaped to receive inverted T-shaped connection 35. In the continuation of slide member 41, femur part 3 consists of a shank portion 45 which extends from slide member at an angle of about 30°. Finally, femur part 3 is terminated by a femur canal insertable portion 47 which will now be more specifically described and which extends from shank portion at an angle of about 15°. This is all well illustrated in FIG. 4 of the drawings.

As shown particularly in FIGS. 1, 2 and 3, femur canal insertable portion 47 comprises a first elongated pyramidal member 49 which extends from shank portion 45. Strictly speaking, member 49 has the shape of a rectangular pyramid, one side 51 being perpendicular to the bottom and base of the pyramid. An elongated trapezoidal member 53 which as shown is shorter and narrower than first elongated pyramidal member 49 and in which both faces are parallel projects from the latter. Finally, there is a second elongated pyramidal member 55 which is shorter and narrower than trapezoidal member 53 and projects from the latter. This particular arrangement of femur canal insertable portion 47 enables it to be embedded in regenerated bone marrow when curing is achieved thereby making sure that the hip prosthesis will not be unlocked from the femur canal.

Finally, as an alternative to the acetabulum part described with reference to FIGS. 1 and 2, reference will be made to FIGS. 5 and 6. In this case, acetabulum part 57 is in the shape of a truncated half sphere without indentations, although, similar indentations as in the case of acetabulum part 1 may also be provided. In acetabulum part 57, there is a flat face 59 which is formed with four triangular openings 61. This particular arrangement promotes the growth of bone tissue through the openings, thereby ensuring a firm placement of part 57 in the acetabulum while preventing it from becoming unlocked therefrom after being in place for a while. To fix acetabulum part 57 in the acetabulum, four screw holes 63 are provided at 45°. It will be noted that in this case buffer member 9 is spaced from the walls of acetabulum part 55 to facilitate the growth of bone cells through openings 61.

I claim:

1. A hip prosthesis to replace a damaged hip-joint, said hip prosthesis to be disposed at one end thereof into a cup-shaped cavity of an acetabulum and at the other end thereof into a femur canal of a person suffering from said damaged hip-joint, said hip prosthesis comprising an acetabulum part and means for tightly engaging said acetabulum part into said acetabulum;

an elongated neck part;

a femur part;

said elongated neck part having an articulation head at one end thereof, said head being shaped to be articulately received in said acetabulum part, and a slidable inverted T-shaped connecting portion which is perpendicular to said neck part and is provided at the other end of said neck part for engagement with said femur part;

said femur part having a femur canal insertable portion formed with means to secure same in said femur canal by being embedded in regenerated bone marrow, and a slide member formed with an inverted T-shaped cavity shaped to slidably receive said inverted T-shaped portion, said inverted T-shaped portion and said slide member being adapted to be secured together by means of screws, to securely connect said elongated neck part to said femur part.

2. A hip prosthesis according to claim 1, wherein said acetabulum part is semi-spherical.

3. A hip prosthesis according to claim 1, wherein said semi-spherical acetabulum part is provided with a plurality of peripheral flanges capable of engaging with said acetabulum.

4. A hip prosthesis according to claim 3, wherein said peripheral flanges are each formed with a plurality of outwardly projecting points, said projecting point forming an angle of between about 30 and 60° with respect to a tangent at the location of a respective projecting point.

5. A hip prosthesis according to claim 4, wherein said outwardly projecting points are regularly distributed along each said flanges.

6. A hip prosthesis according to claim 1, which comprises a buffer member adapted to be fixedly mounted inside said acetabulum part, and to snappingly engage said articulated head.

7. A hip prosthesis according to claim 6, wherein said buffer part is semi-spherical, and provided with a cup-shaped cavity to receive said articulated head.

8. A hip prosthesis according to claim 7, wherein said buffer part is made of a material selected from the group of polyethylene, ceramic and an inert metallic substance.

9. A hip prosthesis according to claim 1, wherein said acetabulum member is made of a titanium containing substance.

10. A hip prosthesis according to claim 1, wherein said femur part comprises a shank portion joining said femur canal insertable portion and said engaging means.

11. A hip prosthesis to replace a damaged hip-joint, said hip prosthesis to be disposed at one end thereof into a cup-shaped cavity of an acetabulum and at the other end thereof into a femur canal of a person suffering from said damaged hip-joint, said hip prosthesis comprising an acetabulum part and means for tightly engaging said acetabulum part into said acetabulum;

an elongated neck part;

a femur part;

said elongated neck part having an articulation head at one end thereof, said head being shaped to be articulately received in said acetabulum part, and slidable connecting means at the other end thereof for engagement with said femur part;

said femur part having a femur canal insertable portion formed with means to secure same in said femur canal by being embedded in regenerated bone marrow, and engaging means to receive said slidable connecting means of said elongated neck part and to securely connect said elongated neck part to said femur part;

said femur part comprising a shank portion joining said femur canal insertable portion and said engaging means; and said femur canal insertable portion comprising a first elongated pyramidal member extending from said shank portion, an elongated trapezoidal member shorter and narrower than said first elongated pyramidal member and projecting from said first elongated pyramidal member, and a second elongated pyramidal member shorter and narrower than said trapezoidal member and tapering down from said shank portion to opposite end thereof, said femur canal insertable portion thereby easily being embedded in said regenerated bone marrow.

12. A hip prosthesis according to claim 11, wherein said femur canal insertable portion angularly extends from said shank portion and said sliding member.

13. A hip prosthesis according to claim 12 wherein said femur canal insertable portion extends from said shank portion at an angle of about 15° and from said sliding member at an angle of about 45°.

14. A hip prosthesis according to claim 13, wherein said acetabulum part comprises a hollow truncated half sphere having a flat face, triangular openings formed in said flat face to permit growth of bone cells into said hollow truncated half sphere, and screw holes along lower edge of said hollow truncated half sphere at about 45°.

15. A hip prosthesis according to claim 14, wherein said buffer member is spaced from walls of said hollow truncated half sphere wherein bone cells can be permitted to grow.

* * * * *